(12) United States Patent
Izmaylov

(10) Patent No.: US 8,245,717 B2
(45) Date of Patent: Aug. 21, 2012

(54) DENTAL STICK

(76) Inventor: Viktor Ivanovich Izmaylov, Moskow Region (RU)

( * ) Notice: Subject to any disclaimer, the term of this patent is extended or adjusted under 35 U.S.C. 154(b) by 697 days.

(21) Appl. No.: 11/596,502

(22) PCT Filed: May 18, 2004

(86) PCT No.: PCT/RU2004/000189
§ 371 (c)(1),
(2), (4) Date: Nov. 13, 2006

(87) PCT Pub. No.: WO2005/110270
PCT Pub. Date: Nov. 24, 2005

(65) Prior Publication Data
US 2008/0023027 A1 Jan. 31, 2008

(51) Int. Cl.
*A61C 15/00* (2006.01)
(52) U.S. Cl. .................................................. 132/329
(58) Field of Classification Search .................. 132/329, 132/321, 328, 309; 33/513; 15/167.1; D28/65; 433/141, 216
See application file for complete search history.

(56) References Cited

U.S. PATENT DOCUMENTS

| | | | |
|---|---|---|---|
| 4,616,667 A | 10/1986 | Tang | |
| D316,163 S * | 4/1991 | Brewer | D28/65 |
| 5,230,356 A * | 7/1993 | Villas | 132/329 |
| 5,735,300 A | 4/1998 | Higgins | |
| 5,775,346 A * | 7/1998 | Szyszkowski | 132/329 |
| 6,085,761 A * | 7/2000 | Inaba | 132/329 |
| 6,158,444 A | 12/2000 | Weihrauch | |

FOREIGN PATENT DOCUMENTS

| | | | |
|---|---|---|---|
| DE | 2541788 | | 4/1976 |
| DE | 2915044 | | 10/1979 |
| SU | 1509065 | | 9/1989 |
| SU | 1627166 | * | 2/1991 |
| WO | WO 96/19155 A3 | | 6/1996 |
| WO | WO 01/47430 A1 | | 7/2001 |

* cited by examiner

*Primary Examiner* — Todd Manahan
*Assistant Examiner* — Brianne Kalach
(74) *Attorney, Agent, or Firm* — Defillo & Associates, Inc; Evelyn A. Defilló

(57) ABSTRACT

The invention relates to medicine, in particular to dentistry. The inventive dental stick comprises a holder (1) provided with oppositely deflected massaging (2) and cleaning (3) elements tapered towards the ends thereof. Said holder is bent so that a fold is formed in the middle section thereof with two symmetrical segments (4) and (5) oppositely shifted with respect to a symmetry axis (6). Said symmetrical segments of the holder (1) have round cross sections (7) reducing away from the middle of the holder towards the massaging elements (2). Said massaging (2) and cleaning (3) elements are formed by two flat faces (8) and (9) which are perpendicular to the holder axis plane. The massaging elements are deflected to the sides which are opposite to the shift of the holder symmetrical segments with respect to the symmetry axis (6). The cleaning elements are provided with roundish-shaped extensions oppositely oriented with respect to the holder axis plane. The surfaces of the massaging elements which are opposite to the extension direction of the corresponding cleaning element are wave-shaped.

4 Claims, 1 Drawing Sheet

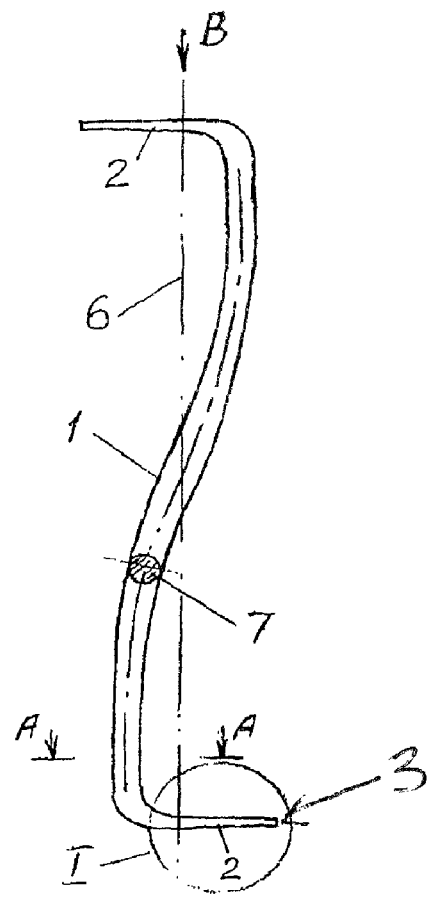
Fig. 1
Fig. 2
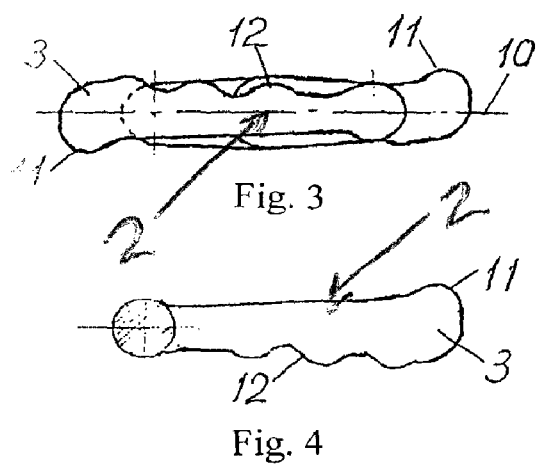
Fig. 3
Fig. 4
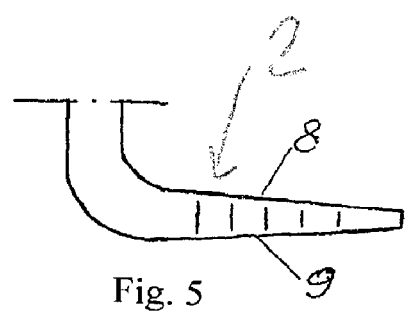
Fig. 5

DENTAL STICK

CROSS REFERENCE TO RELATED APPLICATION

This application is a national stage of PCT/AU2004/001392 filed Oct. 8, 2004 and based upon Australian Application No. AU2003905487 filed Oct. 8, 2003, under the International Convention.

TECHNICAL FIELD OF THE INVENTION AND PRIOR ART

The invention relates to the field of medicine and, more specifically, it relates to the dentistry and is intended for cleaning interdental spaces with simultaneous gingival massage for purposes of improving the hygienic condition of the oral cavity and preventing dental diseases.

Known in the art are dental sticks with cleaning elements deflected from the holder axis (SU 1627166), with a curved holder and pointed cleaning elements (DE 2915044). A common disadvantage of these dental sticks is impossibility or difficulty of simultaneous massage of the gums between teeth.

Also known in the art is a dental stick-activator disclosed in the International Publication WO 1996/019155 (PCT/RU95/00274) containing a holder with oppositely deflected massaging and cleaning elements tapered towards the ends thereof while forming in each massaging a cross-trapezoidal section. The main disadvantage of the known dental stick is difficulty of massaging the gingivae, particularly in more remote gingival sites. Besides, a trapezoidal shape and a variable size of the cross-section of the massaging and cleaning elements complicate the process of production the articles.

SUMMARY OF THE INVENTION

The basic object of the invention is to obtain a dental stick simple in design and providing a possibility of cleaning and massaging interdental spaces with simultaneous massage of the front surface of the gingiva.

This object is attained due to the fact that in a dental stick comprising a holder with cleaning elements tapering towards their ends the holder is bent in the middle section with formation of two symmetric segments displaced relative to the axis of symmetry to the opposite sides, the massaging elements being formed by two flat faces which are perpendicular to the holder axis plane and deflected to the sides which are opposite to the shift of the holder symmetrical segments with respect to the holder axis of symmetry, and the cleaning elements being formed by flat faces are provided with extensions oppositely oriented with respect to the holder axis plane.

The object of the invention is also attained due to the fact that the cross-sections of the symmetrical segments of the holder are made round and reducing away from the middle of the holder towards the massaging elements.

The object of the invention is also attained due to the fact that the surfaces of the massaging elements opposite to the extension direction of the corresponding cleaning element are wave-shaped.

The object of the invention is also attained due to the fact that the symmetrical segments of the holder are arc-shaped, coupled to each other and their convex portions are directed in the opposite directions, or they are rectilinear coupled to each other through a curved section. The object of the invention is also attained due to the fact that the rectilinear sections of the holder are parallel to its axis of symmetry.

The object of the invention is also attained due to the fact that the extensions of the cleaning elements are roundish-shaped.

The technical result from the use of the invention is obtained due to the fact that making the massaging and cleaning elements with two flat faces perpendicular to the holder axis plane considerably simplifies the manufacturing process, and making the holder as a bent article following the jaw shape provides removal of food debris even between last molars with simultaneous gingival massage.

The presence of a wave-shaped surface on each massaging element enables one to perform pulsing pressing on the soft tissues of the gingiva and gingival papilla, thereby causing an excessive blood supply to these areas and, therefore, to increase the massaging efficiency as a whole.

BRIEF DESCRIPTION OF DRAWINGS

The invention is illustrated by drawings, in which:
FIGS. 1, 2 are two projections of the dental stick;
FIG. 3 is a view along the arrow B in FIG. 1;
FIG. 4 is a cross-sectional view along the line A-A in FIG. 1;
FIG. 5 is an enlarged view of the massaging element (fragment I in FIG. 1).

DETAILED DESCRIPTION OF PREFERRED EMBODIMENT OF THE INVENTION

The dental stick comprises a holder 1 with a massaging element 2 and cleaning element 3. The holder 1 is bent with a fold in the middle section to form two symmetrical segments 4 and 5 shifted relative to the axis of symmetry 6 in the opposite sides. The symmetrical segments of the holder 1 are arc-shaped coupled to each other and their convex portions are directed in the opposite directions. The cross-sections 7 of the symmetrical segments of the holder 1 are made round and reducing away from the middle of the holder towards the massaging elements.

The massaging and cleaning elements 2, 3 are tapered in the direction towards the ends of the cleaning elements and have two flat faces 8 and 9 perpendicular to the axis plane 10 of the holder. The massaging elements 2 are deflected in the directions opposite to the shift of the symmetrical segments 4 and 5 of the holder relative to the axis of symmetry 6. The cleaning elements 3 have roundish-shaped extensions 11 which are directed in the opposite sides relative to the axis plane 10 of the holder. The surfaces 12 of the massaging elements opposite to the direction of the extension 11 of an appropriate cleaning element are wave-shaped.

The dental stick may be made of stainless steel or high-strength plastic. All links of the dental stick should be rounded to reduce its internal stress and to exclude the possibility of damage of parodontium tissue.

MODE OF OPERATION OF THE INVENTION

The dental stick is used as follows. One of the symmetrical segments of the holder with the massaging element is clipped by three fingers of the right hand. If in this case the other massaging element is directed downwards, the top right or bottom left sides of the jaw is treated. In the space between the adjacent teeth there are entered the cleaning element 3 and then the massaging element 2 and a few movements are made across the jaw and up-and-down with a slight pressing on the gingiva between the teeth that allows one to remove the food debris and, at the same time, to perform the massage of the gingiva and gingival papilla. After that the dental stick is taken for the other end, and it is performed the treatment of the left half of the top jaw and the right half of the lower jaw.

The invention can be widely used in the dental practice as means of individual hygiene allowing one to reduce inflammatory processes in parodontium tissues, to stop gingiva angiostaxis, to reduce the teeth mobility, to improve vessel trophism and activity of the parodontium nervous system.

Since practically all adult population all over the world suffer from parodontium diseases the scope of production dental sticks is unlimited.

What is claimed is:

1. A dental stick comprising:
    a bent elongated holder having a center axis, a top and bottom surface and two opposing ends formed by arched shape segments that are directed in opposition with respect to the center axis; the arch shaped segments also having a top and bottom surface;
    wherein each arch shaped segment comprises:
        a massaging element formed by two opposing flat faces that extend perpendicularly from the center axis between the top and bottom surfaces and having a wave shaped face located between the flat faces;
        a cleaning element located opposite the wave shaped face, formed by a flat surface that extends to a distal cleaning tip;
    wherein the wave shaped surfaces of each arch shaped segment are located on opposing top/bottom surfaces of the arch shaped segments.

2. The dental stick of claim 1, wherein each massaging element tapers towards the cleaning elements.

3. The dental stick of claim 1, wherein the holder has a cross-section that tapers towards each end.

4. The dental stick according to claim 1, wherein the tip of each cleaning element is made round.

* * * * *